(12) United States Patent
Derksen et al.

(10) Patent No.: US 9,546,301 B2
(45) Date of Patent: Jan. 17, 2017

(54) PROCESS FOR THE PREPARATION OF MULTIFUNCTIONAL POLYCARBODIIMIDES WHICH ARE USED AS CROSSLINKING AGENTS

(71) Applicant: Stahl International B.V., Waalwijk (NL)

(72) Inventors: Andries Johannes Derksen, Nijmegen (NL); Robrecht Leonardus Johannes van der Bruggen, Eindhoven (NL)

(73) Assignee: STAHL INTERNATIONAL B.V., Waalwijk (NL)

( * ) Notice: Subject to any disclaimer, the term of this patent is extended or adjusted under 35 U.S.C. 154(b) by 288 days.

(21) Appl. No.: 13/751,463

(22) Filed: Jan. 28, 2013

(65) Prior Publication Data
US 2013/0144006 A1 Jun. 6, 2013

Related U.S. Application Data

(63) Continuation of application No. PCT/NL2011/050397, filed on Jun. 6, 2011.

(30) Foreign Application Priority Data

Jul. 28, 2010 (NL) ..................................... 2005163

(51) Int. Cl.

| C07F 9/6568 | (2006.01) |
|---|---|
| C08G 18/02 | (2006.01) |
| C08G 18/09 | (2006.01) |
| C08G 18/22 | (2006.01) |
| C08G 18/28 | (2006.01) |
| C08G 18/79 | (2006.01) |
| C08G 73/00 | (2006.01) |
| C08L 75/00 | (2006.01) |
| C08L 79/00 | (2006.01) |
| C08L 75/04 | (2006.01) |
| C09D 175/04 | (2006.01) |
| C09D 179/00 | (2006.01) |

(52) U.S. Cl.
CPC ......... *C09D 179/00* (2013.01); *C07F 9/65685* (2013.01); *C08G 18/025* (2013.01); *C08G 18/095* (2013.01); *C08G 18/227* (2013.01); *C08G 18/283* (2013.01); *C08G 18/289* (2013.01); *C08G 18/2825* (2013.01); *C08G 18/797* (2013.01); *C08G 73/00* (2013.01); *C08L 75/04* (2013.01); *C08L 79/00* (2013.01); *C09D 175/04* (2013.01); *C08L 75/00* (2013.01)

(58) Field of Classification Search
CPC .. C07F 9/65685; C08G 18/095; C08G 18/227; C08G 18/2825; C08G 18/283; C08G 18/289; C08G 18/797; C08G 73/00; C08G 18/025; C08L 75/00; C08L 79/00; C08L 75/04; C09D 179/00; C09D 175/04
See application file for complete search history.

(56) References Cited

U.S. PATENT DOCUMENTS

| 4,118,536 A | 10/1978 | Beardsley et al. |
|---|---|---|
| 5,258,481 A | 11/1993 | Hesselmans et al. |
| 6,566,437 B2 | 5/2003 | Brown |
| 7,439,316 B2 | 10/2008 | Hesselmans et al. |
| 2002/0007001 A1 | 1/2002 | Brown |

FOREIGN PATENT DOCUMENTS

| EP | 0507407 B1 | 6/1996 |
|---|---|---|
| EP | 1162237 A1 | 12/2001 |
| EP | 1598400 A3 | 3/2008 |
| WO | 2005-003204 A2 | 1/2005 |

*Primary Examiner* — Patrick Niland
(74) *Attorney, Agent, or Firm* — Jeffrey D. Myers; Peacock Myers, P.C.

(57) ABSTRACT

A process for the preparation of multifunctional polycarbodiimides, which are used as crosslinking agents, in which the polycarbodiimide is prepared by reacting mono- and polyisocyanates in the presence of a mono- or polyisocyanate that contains one or multiple additional reactive functional groups and in the presence of a carbodiimide catalyst, and thereafter terminating or chain extending the polycarbodiimide chain. Between 0 and 10% of an organic solvent and/or between 0 and 30% of a plasticizer and/or between 0 and 30% of a surface active component is added to the product during, before or after the polycarbodiimide forming reaction and/or the capping reaction and/or the chain extending reaction. Further, the invention relates to a coating mixture in which the polycarbodiimide is used as crosslinking agent and to the cured material obtained with the coating mixture.

14 Claims, No Drawings

PROCESS FOR THE PREPARATION OF MULTIFUNCTIONAL POLYCARBODIIMIDES WHICH ARE USED AS CROSSLINKING AGENTS

CROSS-REFERENCE TO RELATED APPLICATIONS

This application is a continuation application of International Patent Application Serial No. PCT/NL2011/050397, entitled "Process for the Preparation of Multifunctional Polycarbodiimides Which are Used as Crosslinking Agents", to Stahl International B.V., filed on Jun. 6, 2011, and the specification and claims thereof are incorporated herein by reference.

This application claims priority to and the benefit of the filing of Netherlands Patent Application Serial No. 2005163, entitled "Process for the Preparation of Multifunctional Polycarbodiimides Which are Used as Crosslinking Agents", filed on Jul. 28, 2010, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Field of the Invention (Technical Field):

A process for the preparation of multifunctional polycarbodiimides, which are used as crosslinking agents, in which the polycarbodiimide is prepared by reacting mono- and polyisocyanates in the presence of a mono- or polyisocyanate that contains one or multiple additional reactive functional groups and in the presence of a carbodiimide catalyst, and thereafter terminating or chain extending the polycarbodiimide chain. Further, the invention relates to a coating mixture in which the polycarbodiimide is used as crosslinking agent and to the cured material obtained with the coating mixture.

Description of Related Art:

Polycarbodiimides are well known crosslinking agents for aqueous polymers containing carboxylic acid functions. A review of the development of the preparation and the application of polycarbodiimides is described in EP1644428 (U.S. Pat. No. 7,439,316). Of particular interest are the polycarbodiimides that possess additional functional groups that contribute to the crosslinking.

The preparation and application of multifunctional polycarbodiimides as crosslinking agents is described in EP0507407 (U.S. Pat. No. 5,258,481). These crosslinking agents contain carbodiimide groups and at least one other functional group.

Both groups contribute to the crosslinking. A relative large amount (about 50%) of solvent is used in the preparation method because the viscosity would otherwise become too high during the first stage of the preparation of the multifunctional polycarbodiimide crosslinking agent. As a result the crosslinking agent contains a relatively large amount of volatile organic compounds, which is undesired nowadays because of environmental reasons. In addition, the concentration of carbodiimide groups and the concentration of the other reactive groups are apparently relatively low by using this method, so that a relatively high amount of multifunctional polycarbodiimide crosslinking agent is required to obtain a good crosslinking degree of the polymer to be cross-linked.

It is described in the conclusions and examples of U.S. Pat. Nos. 6,566,437 and 4,118,536 how an alkoxysilane functional polycarbodiimide can be prepared from an isocyanate with an alkoxysilane function, but this polycarbodiimide does not contain hydrophilic groups and will as a result not be well dispersible in water or aqueous systems. Moreover, 36% of an organic solvent is used in the example of U.S. Pat. No. 6,566,437 so that the benefits of the present process are not disclosed. An example of U.S. Pat. No. 4,118,536 describes how an alkoxysilane functional carbodiimide can be prepared from an isocyanate with an alkoxysilane function, but the alkoxysilane functional carbodiimide concerned is made in a very low concentration in this example, so that the benefits of the present process are missing.

The object of the present invention is to provide a process in which the disadvantages mentioned above are eliminated.

BRIEF DESCRIPTION OF THE INVENTION

According to the present invention there is provided a process for the preparation of multifunctional polycarbodiimides, which are used as crosslinking agents, comprising:

A. the reaction of a mono- and/or polyisocyanate at 80-180° C. in the presence of 0.05-5 weight percentage of a carbodiimide catalyst, in which a polycarbodiimide or an isocyanate functional polycarbodiimide is formed with a mean value of 1-10 carbodiimide functions B. terminating and/or chain extending the isocyanate functional polycarbodiimide chain, during or after the formation of the polycarbodiimide chain by the addition of 0.05 to 1.0 equivalent, regarding to the isocyanate functions that are not consumed in the formation of the polycarbodiimide chain, of a compound containing a hydrophilic group and one or multiple amine and/or hydroxyl functions, together with, prior to, or followed by capping of the remaining isocyanate functions with a compound containing one or multiple amine and/or hydroxyl functions, in which the compound containing one or more amine and/or hydroxyl functions can also contain an additional functional group, characterized in that in step A 0.5-30 weight percentage of one or multiple mono- and/or polyisocyanates containing one or multiple additional functional groups of which the isocyanate group contributes to the carbodiimide formation is present and further characterized in that 0 to 10% of an organic solvent and/or 0 to 30% of a plasticizer, and/or 0 to 30% of surface active component is added during, before or after the carbodiimide forming reaction and/or the capping reaction and/or the chain extending reaction.

In EP0507407 an additional functionality is incorporated by the terminating reaction of an isocyanate functional carbodiimide oligomer with a hydroxyl or amine functional compound that contains this additional functionality. Surprisingly, it became apparent during the present process that the viscosity of the multifunctional polycarbodiimide is considerably lower if the additional reactive functional group is not incorporated according to the process described in EP0507407 but by means of a carbodiimide forming reaction. This makes it possible to avoid or reduce significantly the use of a solvent while it is still possible to obtain the multifunctional polycarbodiimide with a low enough viscosity so that it can be easily dispersed in water. An additional advantage of incorporating the additional reactive functional group by means of a carbodiimide forming reaction is that the concentration of both, the carbodiimide group and the additional functional group, is higher. The reason is that the mean molecular weight of the resulting polycarbodiimide is lower at the same amount of carbodiimide functions per molecule than the mean molecular weight of a polycarbodiimide for which the additional functional group was incorporated by means of a terminating reaction.

Another advantage of the present invention compared with existing polycarbodiimides with additional functions is that the amount of solvent can be reduced significantly or that the use of a solvent can be avoided completely.

An amount of plasticizer can be used in the present process. The reason is that a mixture of polycarbodiimide with a plasticizer has a lower viscosity than the polycarbodiimide by itself. This improves the ease of use. A plasticizer with some hydrophilic nature is preferred, such as tributoxy ethylphosphate, tetraethylene glycol dimethyl ether or tri-ethylene glycol-mono-2-hexyl-hexanoate, so that the polycarbodiimide together with the plasticizer can be dispersed easily in water or aqueous systems.

The products that are prepared according to the method of the present process can be dispersed easily in water or aqueous polymer dispersions in which they are used because a hydrophilic group has been incorporated into the polymer.

There are several options for the composition of the mono and/or diisocyanate which may be used in the process. The mono-isocyanate may be an isocyanate containing a linear or branched alkyl, alkylene, alkyl-aryl or alkylene-aryl group with 6-25 carbon atoms. For example it may be an alkyl-, cycloalkyl, alkyl-aryl, or arylalkyl functional isocyanate, such as hexylisocyanate, octylisocyanate, undecylisocyanate, dodecylisocyanate, hexadecylisocyanate, octadecylisocyanate, cyclohexylisocyanate, phenylisocyanate, tolylisocyanate, 2-heptyl-3,4-bis(9-isocyanatononyl)-1-pentylcyclohexane.

A further option is that the mono-isocyanate and/or polyisocyanate is the adduct of a polyisocyanate and a hydroxyl- or amine functional compound with a linear or branched alkyl, alkylene, alkyl-aryl or alkylene-aryl group with 4-25 carbon atoms.

A further option is that the mono-isocyanate is an isocyanate containing an alkyl, an alkylene, an alkyl-aryl or an alkylene-aryl group which contains 1-50 fluorine atoms.

Examples of these are fluorophenylisocyanate, fluorotolyliso-cyanate and 3-(trifluoromethyl)phenylisocyanate.

A further option is that the mono-isocyanate and/or polyisocyanate is the adduct of a polyisocyanate and a hydroxyl- or amine functional compound with an alkyl, an alkylene, an alkyl-aryl or an alkylene-aryl group containing 1-50 fluorine atoms.

A further option is that the mono-isocyanate and/or polyisocyanate is the adduct of a polyisocyanate and a hydroxyl functional silicon or amine functional silicon, a hydroxyl alkyl functional silicon or an amino-alkyl functional silicon.

The polyisocyanate which is used for the preparation of the polycarbodiimide is toluene-2,4-diisocyanate, toluene-2,6-diisocyanate and mixtures thereof, is diphenylmethane-4,4-diisocyanate, 1,4-phenylenediisocyanate, dicyclohexyl-methane-4,4'-diisocyanate, 3-isocyanatomethyl-3,5,5-trimethylcyclo-hexylisocyanate, 1,6-hexyldiisocyanate, 1,4-cyclohexyldiiso-cyanate, norbonyldiisocyanate, or a mixture thereof. The polyisocyanates that are preferably used are di-cyclohexylmethaan-4,4'-diisocyanate or 3-isocyanatomethyl-3,5,5-trimethylcyclo-hexylisocyanate.

The mono-isocyanate that contains one or multiple additional reactive functional groups and that contributes to the formation of an isocyanate functional polycarbodiimide is an isocyanate compound with one or multiple reactive groups which is not a carbodiimide, with a reactivity towards functional groups in a polymer or a polymer dispersion, emulsion or solution in water or with a capability for self-condensation or self-addition, directly or after hydrolysis. The reactive functional group can be a halogen; alkenyl; ary-1-alkene; alkynyl; arylalkyn; alkadiene; aldehyde; dialkyl-acetal; dithioacetal; ketone; unsaturated aldehyde; ketone or carboxylic ester; nitrile; imine; alkylalkoxy silane; alkoxy-silane; anhydride; mixed anhydride; oxime-protected diisocy-anate; diketone; ketoester; thioketoester; ketothioester; thioketothioester; or a mixture of one or multiple of such reactive groups; the reactive functional group can also be a reactive ring system or contain such a system. The reactive ring system can be any ring system that can open upon an electrophilic or nucleophilie attack. The reactive ring system can by any three, four, five, six, seven or eight membered ring that contains one or multiple nitrogen and/or oxygen and/or sulphur and/or keto and/or keto-enol functions.

Examples of such reactive ring systems are aziridine, epoxide, thiirane, azirine, oxirene, thiirene, azetidine, oxetane, thietane, beta-lactam, beta-lactone, thiethanon, fu-ran, pyrroline, dihydrofuran, dihydrothiophene, pyrrolidine, tetrahydrofuran, tetrahydrothiophene, oxazolidine, dioxolane, oxathiolane, thiazolidine, imidazoline, dithiolane, pyra-zolidine, pyrazoline, oxazoline, thiazoline, imidazoline, dioxole, oxazolon, pyrrolidone, butyrolactone, thiobutyrolactone, butyrothiolactone, thiobutyrothiolactone, oxazolidone, dioxolane-2-on, thiazolidinone, dihydropyridine, tetrahydro-pyridine, pyran, dihydropyran, tetrahydropyran, succinic acid anhydride, succinimide, thiopyran, dihydrothiopyran, tetrahy-drothiopyran, dihydropyrimidine, tetrahydropyrimidine, hexa-hydropyrimidine, dioxane, morpholine, thiamorpholine, dithiane and triazine.

The mono-isocyanate that contains one or multiple additional reactive functional groups and that contributes to the formation of the isocyanate functional polycarbodiimide is preferably an isocyanate compound that contains a trimethoxysilane, dimethoxymethylsilane or a tri-ethoxysilane group because these alkoxysilane groups contribute effectively to the crosslinking reaction by self-condensation, directly or after hydrolysis.

The mono-isocyanate or poly-isocyanate that contains an additional reactive groups is preferably (3-isocyanato-propyl)trimethoxysilane, (3-isocyanatopropyl)tri-ethoxysilane, or (3-isocyanatopropyl)methyldimethoxysilane.

The carbodiimide catalyst which is used in the process may be any conventional carbodiimide catalyst, but preferably 1-methylphospholene-oxide is used.

The compound containing an hydrophilic group and one or multiple amine and/or hydroxyl functions is a polyethoxy mono- or diol with a molecular weight between 100 and 3000 Dalton, a polyethoxy/polypropoxy mono- or diol with a molecular weight between 100 and 3000-Dalton and an ethoxy/propoxy ratio between 100/0 and 25/75, a polyethoxy mono- or diamine with a molecular weight between 100 and 3000, a polyeth-oxy/polypropoxy mono- or diamine with a molecular weight between 100 and 3000 Dalton and an ethoxy/propoxy ratio between 100/0 and 25/75, a diol or diamine containing a pendant polyalkoxy chain, an hydroxyl- or amine alkylsulphonate, or a dialkylamino-alkyl-alcohol or amine, or a mixture thereof.

The compound that contains one or multiple amine and/or hydroxyl functions together with one or multiple additional reactive functional groups is a compound with one or multiple reactive groups with a reactivity towards functional groups in a polymer or a polymer dispersion, emulsion or solution in water or towards corresponding groups, for example by self-condensation or self-addition.

The reactive functional group can be a halogen; alkenyl; arylalkene; alkynyl; arylalkyn; alkadiene; aldehyde; dialkylacetal; dithioacetal; ketone; unsaturated aldehyde; ketone or carboxylic ester; nitrile; imine; alkylalkoxy silane; alkoxysilane; anhydride; mixed anhydride; oxime-protected diisocyanate; diketone; ketoester; thioketoester; ketothioester; thioketothioester; or a mixture of one or multiple of such reactive groups; the reactive functional group can also be or contain a reactive ring system.

The reactive ring system can be any ring system that can open upon an electrophilic or nucleophilic attack. The reactive ring system can by any three, four, five, six, seven or eight membered ring that contains one or multiple nitrogen and/or oxygen and/or sulphur and/or keto and/or ketoenol functions.

Examples of such reactive ring systems are aziridine, epoxide, thiirane, azirine, oxirene, thiirene, azetidine, oxetane, thietane, beta-lactam, beta-lactone, thiethanon, furan, pyrroline, dihydrofuran, dihydrothiophene, pyrrolidine, tetrahydrofuran, tetrahydrothiophene, oxazolidine, dioxolane, oxathiolane, thiazolidine, imidazoline, dithiolane, pyrazolidine, pyrazoline, oxazoline, thiazoline, imidazoline, dioxole, oxazolon, pyrrolidone, butyrolactone, thiobutyrolactone, butyrothiolactone, thiobutyrothiolactone, oxazolidone, dioxolane-2-on, thiazolidinone, dihydropyridine, tetrahydropyridine, pyran, dihydropyran, tetrahydropyran, succinic acid anhydride, succinimide, thiopyran, dihy-drothiopyran, tetrahydrothiopyran, dihydropyrimidine, tetra-hydropyrimidine, hexahydropyrimidine, dioxane, morpholine, thiamorpholine, dithiane and triazine.

The compounds that contains a reactive proton can be a ring system if this ring system contains a reactive proton such as in 2-methylaziridine, 4-dimethyloxazolidine, thiazolidine and the like. The reactive proton can be present in a hydroxyl compound or an amine compound. These are connected to the additional functional group or reactive ring system directly or by an optional alkyl, cycloalkyl or aryl group, such as in 1-(2-hydroxyethyl)-ethyleneimine, glycidol, N-cyclo-hexyl-3-hydroxy-azetidine, 2-ethyl-3-hydroxyethyl-2-methyl-oxazolidine, 4-ethyl-4-hydroxy-oxazoline, allyl alcohol, methylethylketone oxime, 1-amino-3-(triethoxysilyl)-propane, 1-amino-3-(trimethoxysilyl)-propane. A further option is that the reactive proton is present in a hydroxyl compound or amine compound and that these are connected to an additional functional group directly or by an optional alkyl, cycloalkyl or aryl group on one or multiple additional functional groups. An example is di-(3-trimethoxy-silylpropyl)-amine. Also compounds with two or more reactive protons can be used, such as for example N-(3-trimethoxysilylpropyl)-1,2-diaminoethane.

The plasticizer is a plasticizer from the group of phtalic acid alkylesters, adipic acid alkylesters, sebacic acid alkyl esters, dodecanoic acid alkyl esters, polyesters, phosphate esters, polyethers, polyether-polyesters, fatty acid esters, normal or modified natural or mineral oils, sulphonated oils, ethoxylated oils, epoxidized oils, fatty acids, sulfonamides, fat liquors, lecithine or mixtures thereof. A plasticizer with some hydrophilic nature is preferred, such as tributoxy ethylphosphate, tetraethylene glycol dimethyl ether or triethylene glycol-mono-2-hexyl-hexanoate so that the polycarbodiimide together with the plasticizer can be dispersed easily in water or aqueous systems.

The surface active materials are the conventional surface active ionic or non-ionic agents that are used in the coatings industry with the exception of the hydroxyl or amine functional types. The reaction of the isocyanate functional polycarbodiimide with the compound that contains a hydrophilic group together with one or multiple hydroxyl or amine groups can be catalyzed by conventional catalysts used in the polymer industry.

The invention further relates to a coating mixture comprising the polycarbodiimide as crosslinking agent and a polymer dispersed in water, which polymer contains carboxylic acid functions and which may contain a solvent.

Examples of these polymers are polyurethanes, acrylate or methacrylate polymers or copolymers, polyvinylacetates, latexes.

Further, the coating mixture may contain organic solvents or conventional additives, such as emulsifiers, colorants, pigments, wetting agents, leveling agents, silicones, fillers, plasticizers, matting agents.

Finally the invention extends to the cured material which is obtained by applying the coating mixture to a substrate and evaporation of the water and, if present, the solvent. Suitable substrates are for example: leather, artificial leather, plastics such as polyurethanes, polyacrylates, polyethylene, polypropylene, PVC or polyester, paper, paper board, textile, non-woven, cloth, foam, wood, glass, metal, asphalt, stone, concrete.

The present invention is further illustrated by the following examples to which the invention is however not limited. It goes without saying that numerous other embodiments are possible, all within the scope of protection.

EXAMPLES

Examples 1-26

The Preparation of Multifunctional Polycarbodiimides

Under a nitrogen atmosphere a mixture of diisocy-anate, octadecylisocyanate (in the following indicated as ODIC), and an isocyanate with an additional functional group as indicated in Table 1 and 1-methylphospholene-1-oxide was heated to 140° C. while stirring and heating was continued until a NCO-content was obtained corresponding to the desired theoretical amount of carbodiimide functions in the polymer, as indicated in Table 1. The reaction time was 4 to 8 hrs. Then the mixture was cooled to 90-100° C. Hydroxyl functional compounds were added as indicated in Table 1. 0.01 Weight % of dibutyl tin laureate or bismuth carboxylate was added as catalyst and the mixtures were reacted further at 90-100° C. until the NCO-content was decreased such that this NCO-content corresponds with reacting away of the hydroxyl functional compounds. Amine functional compounds were added subsequently or simultaneously as indicated in Table 1. The completeness of the reaction was checked by infrared analysis. Plasticizers were added during or after the process steps described above, as indicated in Table 1. Samples were subjected to a stability test at 50° C. Every 2 weeks the carbodiimide amount was checked. The products were stable for at least 8 weeks at 50° C.

TABLE 1

| Example | Diisocyanate | Diisocyanate (g) | ODIC (g) | X-NCO[c] (g) | MPEG-750[d] (g) | MPEG-350[e] (g) | HDA[f] (g) | OA[g] (g) | Silane-NH[h] (g) | Plasticizer (g) | Theoretical amount of carbodiimide functions in polymer | Viscosity of product at 20° C. (mPa·s) |
|---|---|---|---|---|---|---|---|---|---|---|---|---|
| 1 | IPDI[a] | 200 | 212 | 111[k] | | 64 | | | | | 2.0 | 600 |
| 2 | IPDI | 200 | 89 | 125[k] | | 105 | | | | | 2.0 | 1250 |
| 3 | HMDI[b] | 200 | 75 | 105[k] | | 91 | | | | | 2.0 | 1900 |
| 4 | IPDI | 200 | | 115[k] | | 113 | 61 | | | | 2.0 | 6500 |
| 5 | IPDI | 200 | | 77[k] | | 105 | | | | | 3.0 | 38200 |
| 6 | IPDI | 200 | | 77[k] | | 87 | | | | 23 TBEP[i] | 3.0 | 14400 |
| 7 | IPDI | 200 | | 57[k] | | 87 | | | | | 4.0 | 680000 |
| 8 | IPDI | 200 | | 57[k] | | 87 | | | | 86 TBEP[i] | 4.0 | 156000 |
| 9 | IPDI | 200 | 38 | 26 | | 90 | | | | | 3.5 | 43000 |
| 10 | IPDI | 200 | | 115[k] | | 113 | | | | 86 TBEP[i] | 2.0 | 1500 |
| 11 | HMDI | 200 | | 79[k] | | 79 | | | | | 2.0 | 15000 |
| 12 | IPDI | 200 | | 92[k] | | 61 | 12 | | 77 | | 2.0 | 19000 |
| 13 | IPDI | 200 | | 92[k] | | 61 | 12 | | 77 | 101 TG[j] | 2.0 | 750 |
| 14 | IPDI | 200 | | 92[k] | 38 | | | | 77 | | 2.0 | 42000 |
| 15 | IPDI | 200 | | 92[k] | 38 | | | | 77 | 104 TG[j] | 2.0 | 1000 |
| 16 | IPDI | 200 | | 92[k] | | 55 | | 29 | 31 | | 2.0 | 18000 |
| 17 | IPDI | 200 | | 92[k] | | 55 | | 29 | 31 | 92 TG | 2.0 | 800 |
| 18 | IPDI | 200 | | 92[k] | 51 | | 64 | | 40 | | 2.0 | 22000 |
| 19 | IPDI | 200 | | 92[k] | 51 | | 64 | | 40 | 102 TG | 2.0 | 900 |
| 20 | IPDI | 200 | | 103[k] | 52 | | | 24 | 71 | | 1.8 | 37000 |
| 21 | IPDI | 200 | | 103[k] | 52 | | | 24 | 71 | 130 TG | 1.8 | 600 |
| 22 | IPDI | 200 | | 103[k] | 52 | 39 | | | 79 | | 1.8 | 20000 |
| 23 | IPDI | 200 | | 103[k] | 52 | 39 | | | 79 | 136 TG | 1.8 | 500 |
| 24 | IPDI | 200 | | 103[k] | 52 | 39 | | | 79 | 136 TBEP | 1.8 | 1300 |
| 25 | IPDI | 200 | | 123[l] | 52 | 39 | | | 79 | | 1.8 | 24000 |
| 26 | IPDI | 200 | | 55[m] | 52 | 39 | | | 79 | | 1.8 | 32000 |
| 27 | IPDI | 200 | | 0 | | 52 | | | 153 | | 2.0 | 2400000 |

[a] IPDI is 3-isocyanatomethyl-3,5,5-trimethlylcyclohexylisocyanate;
[b] HMDI is dicyclohexylmethaan-4,4-diisocyanate;
[c] X-NCO is an isocyanaat with an additional functional group, specified further in foot notes;
[d] MPEG750 is a polyehtylene glycol monomethyl either that has a mean molecular weight of 750;
[e] MPEG350 is a polyethlene glycol monomethyl ether that has a mean molecular weight of 350;
[f] HDA is hexadecylalcohol;
[g] OA is 1-octanol;
[h] Silane-NH is di-(3-trimethoxy-silylpropyl amine;
[i] TBEP is tributoxy-ethylphosphate;
[j] TG is tetraethylene glycol dimethylether;
[k] The isocyanate with additional functional group is (3-isocyanatopropyl)trimethoxysilane;
[l] The isocyanate with additional functional group is (3-isocyanatopropyl-ethoxysilane;
[m] The isocyanate with additional functional group is methacryloyl isocyanate

Example 27

Comparative Example

The Preparation of a Multifunctional Polycarbodiimide not Using an Isocyanate that Contains an Additional Functional Group Under a nitrogen atmosphere a mixture of diisocy-anate, as indicated in Table 1, and 1-methylpholene-1-oxide was heated to 140° C. while stirring and heating was continued until a NCO-content was obtained corresponding to the desired theoretical amount of carbodiimide functions in the polymer, as indicated in Table 1. The reaction time was 4 to 8 hours. Then the mixture was cooled to 90-100° C. A hydroxyl functional compound was added as indicated in Table 1. 0.01 Weight % of dibutyl tin laureate was added as catalyst and the mixtures were reacted further at 90-100° C. until the NCO-content was decreased such that this NCO-content corresponds with reacting away the hydroxyl functional compounds.

Subsequently an amine functional compound was added as indicated in Table 1. The completeness of the reaction was checked by infrared analysis.

Comparing the viscosity of Example 27 with the viscosities of Examples 1 to 4 and 10 to 26 demonstrates that the viscosities of Examples 1 to 4 and 10 to 26 are much lower than the viscosity of Example 27 while the theoretical amount of carbodiimide functions in the polymer is the same. Also the viscosities of Examples 5 and 7 are much lower than the viscosity of Example 27 while the theoretical amount of carbodiimide functions in the polymer is higher in Examples 5 and 7 than in Example 27.

Example 28

Testing of the products from Examples 2, 12, 13, 15, 19, 23 and 24 as crosslinker in a polyurethane dispersion with the product from Example 27 as comparative example. 6 weight % of the products from Examples 2, 12, 13, 15, 19, 23 and 24 were mixed with RU-13-085 (a polyurethane dispersion of +Stahl Europe) or with a top coat formulation (a mixture comprising several polyurethane dispersions of Stahl Europe). In case of comparative Example 27 first a 1:1 dilution in a solvent was made so that the processibility is improved and subsequently 12 weight % of this dilution was mixed with RU-13-085 or a top coat formulation. Each dispersion was, with a thickness of 200 μm, applied on a glass sheet and the glass sheet with the applied film on it was dried for 1 day at room temperature and subsequently for 1 hour at 80° C. in an oven. Samples of the dried film were subjected to a solvent uptake test with ethanol or MEK (methyl-ethylketone, or 2-butanone) as solvent. In this test pieces of dried and weighted film are immersed into ethanol or MEK for 1 hour and then the increase of the weight of the film is determined.

The weight increase in this solvent uptake test is a measure for the crosslinking in which a lower increase of weight indicates a higher degree of crosslinking. Further, the mechanical properties and the elongations of the films were measured with a MTS Synergy 200 apparatus. The mechanical properties are a measure for the crosslinking in which a larger stress value at a certain strain indicates a higher degree of crosslinking. The results of the tests are presented in Table 2.

The results show that the crosslinking with the crosslinking agent of Examples 2, 12, 13, 15, 19, 23 and 24 is of a comparable degree as with comparative Example 27, which is demonstrated by the comparable strain in the film which is obtained when the film is stretched and by the comparable weight increase when the films are immersed in ethanol or MEK.

TABLE 2

| Poly-urethane dispersion | cross-linker used of Example | Mechanical properties (MPa)[a] | | Elong-ation[b] % | Weight Increase Ethanol[c] | Weight Increase MEK[d] |
|---|---|---|---|---|---|---|
| | | M-100 | M-200 | | | |
| RU-13-085 | None | 5.5 | 8.6 | 570 | 88 | Lost op |
| RU-13-085 | 2 | 8.5 | 15.9 | 290 | 27 | 80 |
| RU-13-085 | 12 | 11.6 | 23.7 | 215 | 27 | 72 |
| RU-13-085 | 13 | 9.5 | 20.2 | 245 | 24 | 63 |
| RU-13-085 | 23 | 9.8 | 20.5 | 250 | 25 | 55 |
| RU-13-085 | 24 | 8.1 | 19 | 285 | 25 | 55 |
| RU-13-085 | 27 | 12.1 | 25.2 | 220 | 27 | 56 |
| Top coat | None | 2.8 | 3.9 | 225 | 53 | 63 |
| Top coat | 15 | 3.0 | — | 190 | 2 | 3 |
| Top coat | 19 | 2.8 | — | 165 | 10 | 4 |
| Top coat | 27 | 3.6 | — | 170 | 6 | 6 |

[a]MPa is megapascal ($10^6$ Nm$^{-2}$). The mechanical properties were measured on a MTS Synergy 200 apparatus. The values at M-100 and M-200 are strains of the films when they are stretched at respectively 100% and 200%.
[b]The elongation is the maximum elongation at the moment that the film breaks, measured on a MTS Synergy 200 apparatus.
[c]Weight increase is the % weight increase of the film as result of immersing into ethanol.
[d]Weight increase is the % weight increase of the film as result of immersing into MEK (methylethylketone, or 2-Butanone).

What is claimed is:

1. A process for the preparation of water-dispersible multifunctional polycarbodiimides to be used as crosslinking agents, comprising:
   A. the reaction of a mono- and/or polyisocyanate at 80-180° C. in the presence of a carbodiimide catalyst, in which a polycarbodiimide or an isocyanate functional polycarbodiimide is formed with a mean value of 1-10 carbodiimide functions;
   B. terminating and/or chain extending the isocyanate functional polycarbodiimide chain, during or after the formation of the polycarbodiimide chain by the addition of 0.05 to 1.0 equivalent, regarding to the isocyanate functions that are not consumed in the formation of the polycarbodiimide chain, of a compound containing a hydrophilic group and one or multiple amine and/or hydroxyl functions, together with, prior to, or followed by capping of the remaining isocyanate functions with a compound containing one or multiple amine and/or hydroxyl functions, in which the compound containing one or multiple amine and/or hydroxyl functions can also contain an additional functional group, where in step A one or multiple mono- and/or polyisocyanates containing one or multiple additional functional groups, of which the isocyanate group contributes to the carbodiimide formation is present, at least one of said additional functional groups being selected from the group consisting of: halogen; alkenyl; arylalkene; alkynyl; arylalkyn; alkadiene; aldehyde; dialkylacetal; dithioacetal; ketone; unsaturated aldehyde; ketone; ketone ester; carboxylic ester; nitrile; imine; alkylalkoxy silane; alkoxysilane; anhydride; mixed anhydride; oxime-protected diisocyanate; diketone; ketoester; thioketoester; ketothioester; and thioketothioester.

2. A process according to claim 1, wherein said mono- and/or polyisocyanate that contains an additional functional group contains a trimethoxysilane, dimethoxymethylsilane or a tri-ethoxysilane as additional reactive functional group.

3. A process according to claim 1, wherein said mono- and/or polyisocyanate that contains an additional functional group contains as additional reactive functional group a three, four, five, six, seven or eight membered ring that contains one or multiple nitrogen and/or oxygen and/or sulphur and/or keto and/or keto-enol functions.

4. A process according to claim 1, wherein said mono- and/or polyisocyanate that contains an additional functional group is (3-isocyanato-propyl)trimethoxysilane, (3-isocyanatopropyl)tri-ethoxysilane or (3-isocyanatopropyl)methyl-dimethoxysilane.

5. A process according to claim 1, wherein the polycarbodiimide crosslinker contains no solvent.

6. A process according to claim 1, wherein the polycarbodiimide crosslinker contains no plasticizer.

7. A process according to claim 1, wherein the plasticizer is a phosphate ester, polyetherpolyester or a polyether.

8. A process according to claim 1, wherein the compound containing one or multiple amine and/or hydroxyl functions that can also contain an additional functional group contains an additional functional group that is an additional reactive functional group selected from the group consisting of: a halogen; alkenyl; arylalkene; alkynyl; arylalkyn; alkadiene; aldehyde; dialkylacetal; dithioacetal; ketone; unsaturated aldehyde; ketone ester; carboxylic ester; nitrile; imine, alkyloxy silane; alkoxysilane; anhydride; mixed anhydride; oxime-protected diisocyanate; diketone; ketoester; thioketoester; ketothioester; and thioketo-thioester.

9. A process according to claim 8, wherein the additional reactive functional group in the compound that contains one or multiple amine and/or hydroxyl functions together with one or multiple additional reactive functional groups is a trimethoxysilane, a triethoxysilane, an epoxide; an aziridine or an oxazolidine group.

10. A process according to claim 1, wherein the polyisocyanate is dicyclohexylmethane-4, 4'-diisocyanate or 3-isocyanatomethyl-3,5,5-trimethyl-cyclohexylisocyanate.

11. A process according to claim 1, wherein the compound containing an hydrophilic group and one or more amine and/or hydroxyl functions is a polyethoxy mono- or diol with a molecular weight between 100 and 3000 Dalton, a polyethoxy mono- or diamine with a molecular weight between 100 and 3000, a diol or diamine containing a pendant polyalkoxy chain, an hydroxyl- or amine alkylsulfonate, or a dialkylamino-alkyl-alcohol or amine, or a mixture thereof, wherein all molecular weights are number average molecular weights.

12. A process according to claim 1, wherein 0.05 to 0.30 equivalents, regarding to the polyisocyanates, of a mono- or polyol or a mono- or polyamine are added during, before or after the formation of the polycarbodiimide chain, which mono- or polyol or mono- or polyamine is a mono- or polyhydroxy alkane, a polyether mono- or polyol, a polyester polyol, a polycarbonate polyol, a polycaprolactam polyol, a mono- or polyamino alkane, or a polyether mono- or polyamine.

13. A process according to claim 1, wherein an organic solvent and/or a plasticizer and/or a surface active component is added, during, before or after the carbodiimide forming reaction and/or the capping reaction and/or the chain extending reaction.

14. A process according to claim 1, wherein no surface active component is added, during, before or after the carbodiimide forming reaction and/or the capping reaction and/or the chain extending reaction.

* * * * *